United States Patent [19] [11] 3,960,861
Danilewicz et al. [45] June 1, 1976

[54] 2 (OR 4) AMINO 4 (OR 2) N-HETERO QUINAZOLINES

[75] Inventors: John Christopher Danilewicz, Ash; John Edward Glyn Kemp, Canterbury; James Robert Wright, Deal, all of England

[73] Assignee: Pfizer Inc., New York, N.Y.

[22] Filed: Sept. 5, 1973

[21] Appl. No.: 394,491

[30] Foreign Application Priority Data
Sept. 9, 1972 United Kingdom............. 41992/72

[52] U.S. Cl.................. 260/256.4 Q; 260/239 BB; 260/287 D; 260/326.1; 424/251
[51] Int. Cl.$^2$....................................... C07D 239/95
[58] Field of Search............. 260/256.4 Q, 256.5 R

[56] References Cited
UNITED STATES PATENTS

| | | | |
|---|---|---|---|
| 2,591,545 | 4/1952 | Hepworth | 260/256.5 R |
| 2,945,859 | 7/1960 | Hitchings et al. | 260/256.4 Q |
| 3,155,572 | 11/1964 | Rogers et al. | 260/256.5 R |
| 3,635,979 | 1/1972 | Hess | 260/256.4 Q |
| 3,769,286 | 10/1973 | Hess | 260/256.4 Q |
| 3,833,584 | 9/1974 | Gabel et al. | 260/256.4 Q |

FOREIGN PATENTS OR APPLICATIONS
1,131,126  10/1968  United Kingdom.......... 260/256.4 Q OTHER PUBLICATIONS
Theiling et al., J. Am. Chem. Soc., Nov., 1951 vol. 74, pp. 1834–1836.

*Primary Examiner*—Raymond V. Rush
*Assistant Examiner*—David E. Wheeler
*Attorney, Agent, or Firm*—Connolly and Hutz

[57] ABSTRACT

A series of novel 2-amino and 4-aminoquinazoline derivatives have been prepared, including their acid addition salts. These derivatives all possess a single nitrogen-containing benzo-fused heterocyclic ring moiety at either the 4- or 2- positions of the molecule, respectively, with the ring moiety being attached through the nitrogen atom to the aforesaid quinazoline nucleus. Such compounds are useful in therapy as highly potent antihypertensive agents. Methods for their preparation are described in detail, including various synthetic routes leading to the required novel intermediates.

20 Claims, No Drawings

2 (OR 4) AMINO 4 (OR 2) N-HETERO QUINAZOLINES

BACKGROUND OF THE INVENTION

This invention relates to various new and useful amino-quinazoline compounds, and to their chemical method of preparation. More particularly, it is concerned with a novel series of 2-amino-4-substituted quinazolines and 4-amino-2-substituted quinazolines and their pharmaceutically acceptable acid addition salts, which are of especial value in medicine in view of their beneficial therapeutic properties.

In the past, various attempts have been made in the field of organic medicinal chemistry to obtain new and useful antihypertensive agents. For instance, in U.S. Pat. No. 3,511,836, issued May 12, 1970, there are disclosed various 2,4-diamino-6,7-dimethoxyquinazoline compounds useful for these purposes. However, in the search for still newer and better or more improved antihypertensive agents, little is known about the effect of replacing one of the amino groups on the quinazoline nucleus with a single nitrogen-containing benzo-fused heterocyclic ring moiety, whereby the single nitrogen in the ring serves as the sole hetero-element as well as the linking group.

SUMMARY OF THE INVENTION

In accordance with the present invention, it has now been rather surprisingly found that various aminoquinazoline compounds of the above type are extremely useful when employed in therapy as antihypertensive agents. More specifically the novel compounds of this invention are those selected from the class of the general formula:

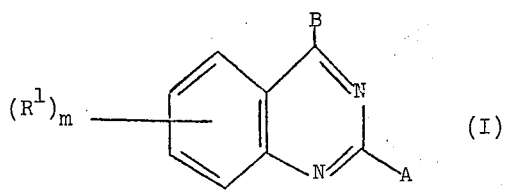

(I)

and the pharmaceutically acceptable acid addition salts thereof, wherein $(R^1)_m$ represents from one to three substituents, each $R^1$ being hydroxyl, benzyloxy or lower alkoxy and m being an integer of from 1 to 3, or two of the moieties $R^1$ when taken together form a lower alkylenedioxy group directly attached to adjacent positions of the benzene-ring portion of the quinazoline nucleus; and one of A and B represents an amino group, while the other represents a benzo-fused heterocyclic ring moiety of the formula

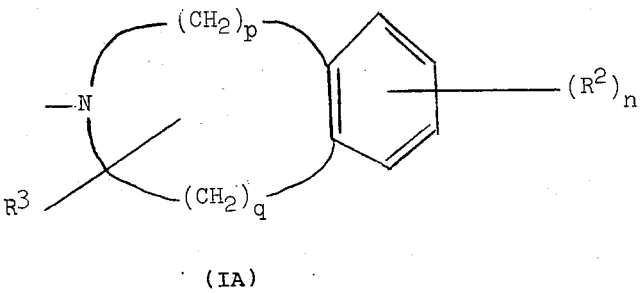

(IA)

wherein $(R^2)_n$ represents from one to three substituents, each $R^2$ being hydroxyl, lower alkoxy, lower alkenoxy, phenoxy, pyridyloxy, nitro, amino, lower alkanoamido, benzenesulfonamido, furoamido or lower alkoxycarbonylamino, n being an integer of from one to three, with the proviso that n can only be 1 when $R^2$ is nitro, amino, lower alkanoamido, benzenesulfonamido, furoamido or lower alkoxycarbonylamino, or two of the moieties $R^2$ when taken together form a lower alkylenedioxy group directly attached to adjacent positions of the benzene-ring portion of the benzo-fused heterocyclic ring moiety; $R^3$ is hydrogen or lower alkyl directly attached to any one of the substitutable carbon atoms of the heterocyclic portion of the benzo-fused heterocyclic ring moiety; and p and q are each 0 to 4 with the proviso that p plus q equals 2 to 4. The term "lower" as applied to a substituent group means such a group containing from one to four carbon atoms. These novel compounds all possess antihypertensive activity to a rather significantly high degree and therefore are extremely useful in the treatment of hypertensive conditions, in addition to being key regulators of the cardiovascular system as well.

Of especial interest in this connection are the preferred compounds of the invention which have the structural formula:

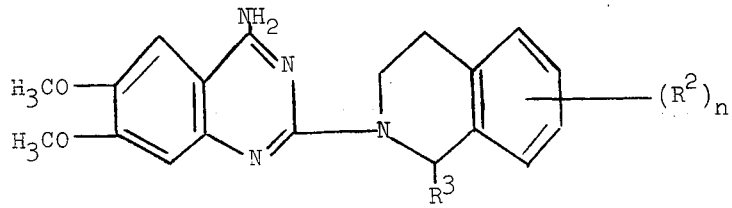

and their pharmaceutically acceptable acid addition salts, wherein $(R^2)_n$ represents 6,7-di-lower alkoxy, 7,8-di-lower alkoxy or 6-methoxy-7-allyloxy and $R^3$ is hydrogen or methyl. Typical member compounds of the preferred class include such 6,7- or 7,8-disubstituted 4-amino-6,7-dimethoxy-2-(1,2,3,4-tetrahydroisoquinolin-2-yl)-quinazolines as 4-amino-6,7-dimethoxy-2-(6,7-dimethoxy-1,2,3,4-tetrahydroisoquinolin-2-yl)quinazoline, 4-amino-6,7-dimethoxy-2-(7,8-dimethoxy-1,2,3,4-tetrahydroisoquinolin- 2-yl)quinazoline, 4-amino-6,7-dimethoxy-2-(6-ethoxy-7-methoxy-1,2,3,4-tetrahydroisoquinolin-2-yl)quinazoline, 4-amino-6,7-dimethoxy-2-(7-isopropyloxy-6-methoxy-1,2,3,4-tetrahydroisoquinolin-2-yl)-quinazoline, 4-amino-6,7-dimethoxy-2-(6,7-diethoxy-1,2,3,4-tetrahydroisoquinolin-2-yl)quinazoline, 4-amino-6,7-dimethoxy-2-(6,7-dimethoxy-1-methyl-1,2,3,4-tetrahydroisoquinolin-2-yl)-quinazoline, 4-amino-6,7-dimethoxy-2-(7-ethoxy-6-methoxy-1,2,3,4-tetrahydroisoquinolin-2-yl)quinazoline and 4-amino-6,7-dimethoxy-2-(7-allyloxy-6-methoxy-1,2,3,4-tetrahydroisoquinolin-2-yl)quinazoline, and their hydrochloride acid addition salts. These particular compounds are all highly potent as regards antihyptertensive activity.

DETAILED DESCRIPTION OF THE INVENTION

The compounds of the invention may be prepared in a number of ways, including the following:

1. All the compounds of the invention other than those in which $(R^2)_n$ is or contains an amino group may be prepared by reacting an appropriately substituted 2,4-dichloroquinazoline of the formula

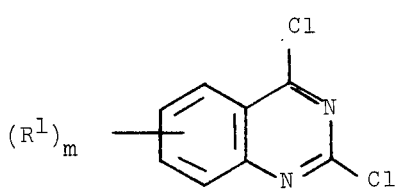

(II)

with ammonia and an appropriately substituted benzo-fused heterocyclic base of the formula

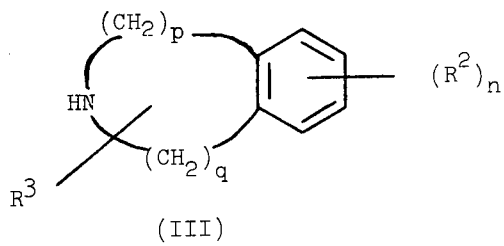

(III)

in the order appropriate for the production of a compound of the desired formula previously indicated, viz.,

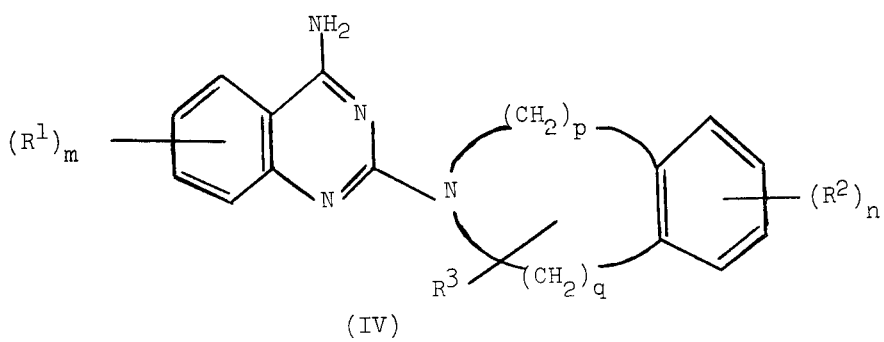

(IV)

or

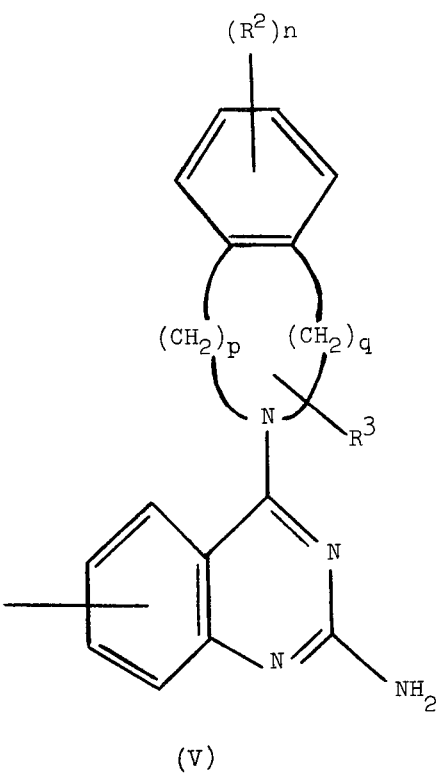

(V)

When ammonia is the first reagent to be reacted with the compound of the formula (II), a compound of the formula (IV) is produced, and similarly, when the reverse order of reagents is used, the product is of formula (V).

The reaction between an appropriately substituted 2,4-dichloroquinazoline of the formula (II) or an appropriately substituted 2-chloro-4-(benzo-fused heterocyclic)-substituted quinazoline and ammonia is suitably performed by maintaining the reagents in a polar organic solvent, e.g., chloroform or ethanol, within the temperature range from about room temperature (~25°C.) to about 100°C. in an autoclave over a period of several hours. The product is typically isolated by either collecting the precipitate via filtration and then washing with water, or else by evaporating the reaction mixture in vacuo to dryness and then extracting the residue with a suitable organic solvent, e.g., methylene chloride, in the presence of water, and subsequently evaporating the separated organic layer to dryness while under reduced pressure. In either case, the crude solid product may then be crystallized from a suitable solvent, e.g., ethanol, to afford the pure free base product. If desired, when the product is a compound of the formula (V), an acid addition salt may be prepared from the crude or pure free base product by the conventional technique of reacting the free base with the acid in an inert organic solvent, e.g., by mixing alcoholic or ethereal solutions of both reagents together, and then collecting the resultant precipitate by means of filtration.

An appropriately substituted 2,4-dichloroquinazoline of the formula (II), or an appropriately substituted 4-amino-2-chloroquinazoline, is suitably reacted with a benzo-fused heterocyclic compound of the formula (III) under basic conditions suitable for the elimination of hydrogen chloride between the two molecules. Various procedures may be used for effecting this reaction, depending upon the nature of the reagent employed. For instance, the two reagents may be dissolved in a suitable organic solvent, like 2-ethoxyethanol or dimethylacetamide, and refluxed or even maintained at room temperature in the presence of a base, e.g., triethylamine or 1-ethylpiperidine, or they may be heated in a suitable solvent such as ethanol in an autoclave at about 160°–200°C. for a period of 8 to 72 hours, e.g., for 16 hours in the presence of a base of the kind exemplified above. The product is typically isolated and purified by evaporating the reaction solution in vacuo to dryness and recrystallizing the resultant crude solid product from a suitable solvent, e.g., ethanol. If desired, when the product is a compound of the formula (IV), an acid addition salt may be prepared by the conventional technique as hereinbefore described.

2. Compounds of the formula (I) in which $(R^2)_n$ is or contains one or more alkoxy, alkenoxy or aryloxy groups may be prepared from the corresponding compounds in which $(R^2)_n$ is or contains one or more hydroxyl groups by conversion of the phenol to its sodium salt, e.g., by using sodium hydride or sodium methoxide in methanolic solution, and then reacting the latter salt with an appropriate organic halide in a suitable organic solvent like dimethylacetamide.

3. Compounds of the formula (I) in which $(R^2)_n$ is or contains an amino group may be prepared from the compounds of the formula (I) in which $(R^2)_n$ is or contains a nitro group by reduction of any such nitro group to an amino group, for example, by hydrogenation in the presence of a catalyst, e.g., Raney nickel, or by reaction with stannous chloride in hydrochloric acid solution.

4. Compounds of the formula (I) in which $(R^2)_n$ is or contains an acylamino group may be prepared from compounds of the formula (I) in which $(R^2)_n$ is or contains an amino group by conventional acylation procedures, for example, by using as the acylating agent the appropriate acyl chloride, with the amino compound dissolved in a suitable organic solvent, e.g., dichloromethane, which also contains base like triethylamine.

5. Compounds of the formula (I) in which $(R^2)_n$ is or contains a lower alkoxycarbonylamino group may be prepared from compounds of the formula (I) in which $(R^2)_n$ is or contains an amino group by reaction with the appropriate lower alkyl chloroformate, for example, by refluxing the reagents together in a suitable organic solvent, such as chloroform in the presence of a base, like triethylamine, for a period of several hours.

6. Compounds of the formula (I) in which $(R^1)_m$ is or contains one or more hydroxyl groups may be prepared from compounds of the formula (I) in which $(R^1)_m$ is or contains one or more benzyloxy groups by removal of any such benzyloxy group, suitably by hydrogenation in the presence of a catalyst, e.g., palladium-on-charcoal, in an acetic acid solution.

The substituted 2,4-dichloroquinazolines of the general formula (II) involved in the reaction described in Method (1), from which all the compounds of the invention are ultimately derived, as well as the corresponding 4-amino-2-chloroquinazolines derived therefrom, are described in British Pat. No. 1.156,973 and may be prepared by the methods described therein. The other starting materials of the general formula (III) may be prepared by well-documented methods appropriate to the nature of the benzo-fused heterocyclic nuclei, for example, as follows:

i. The indolines, of the general formula:

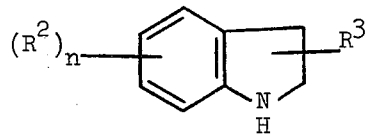

may be prepared by reduction of the corresponding substituted indoles, e.g., by hydrogenation over copper chromite catalyst at 179°–190°C. and 250 atmospheres pressure [Adkins and Coonradt, *Journal of the American Chemical Society*, Vol. 63, p. 1563 (1941)]; by successive reaction of the appropriately substituted o-nitrophenylethyl bromide with a solution of stannous chloride in hydrochloric acid at room temperature and then with hot aqueous sodium hydroxide solution (Adkins and Coonradt, ibid.); by nitration of the appropriately substituted β-phenethyl alcohol and subsequent reduction of the o-nitrophenyl derivative with zinc dust and calcium chloride solution to yield the corresponding o-amino compound, followed by ring closure in the presence of hydrochloric acid at 130°–140°C. for a period of 5 hours and then, liberation of the resulting indoline product from its hydrochloride salt by the use of appropriate alkali [Sabetay, Bléger and Lestrange, *Bulletin de la société chimique de France* [4], Vol. 49, p. 3 (1931) and Bennett and Hafez, *Journal of the Chemical Society* (London), p. 287 (1941)]; or by conversion of the appropriately substituted oxindole to the corresponding thio-oxindole with phosphorus pentasulfide and then electrolytic reduction of the thio-oxindole ring using a lead cathode (Stollé's route).

ii. The isoindolines, of the general formula:

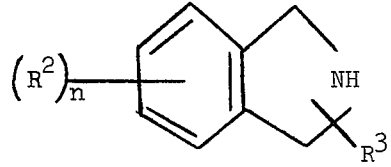

may be prepared by reaction of the appropriately substituted o-xylylene dibromide with ammonia [v. Braun and Nelken, *Chemische Berichte*, Vol. 55, p. 2059 (1922)]; by reaction of such an o-xylylene dibromide with p-toluenesulfonamide and subsequent treatment of the product with concentrated aqueous potassium hydroxide solution [Fenton and Ingold, *Journal of the Chemical Society* (London), p. 3295 (1928)]; by lithium aluminum hydride reduction of the appropriately substituted N-benzylphthalimide (prepared from the appropriate potassium phthalimide or from phthalic anhydride and benzyl chloride or benzylamine, respectively), followed by hydrogenolysis of the benzyl moiety using palladium-on-charcoal as catalyst [Neumeyer, *Journal of Pharmaceutical Sciences*, Vol. 53, p. 981 (1964)], or by hydrogenolysis of the benzyl or benzhydryl moiety of the appropriately substituted N-benzyl or N-benzhydrylisoindoline (prepared from the appropriate o-xylylene dichloride and benzylamine or benzhydrylamine, respectively), via palladium-on-charcoal as catalyst.

iii. The 1,2,3,4-tetrahydroquinolines, of the general formula:

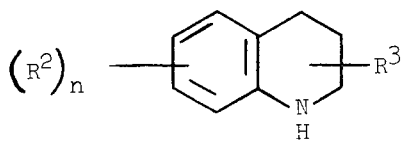

may be prepared by controlled catalytic reduction of the corresponding substituted quinolines, e.g., using W-6 Raney nickel catalyst in alcohol at room temperature (~25°C.) and 1–3 atmospheres pressure [Adkins and Billica, *Journal of the American Chemical Society*, Vol. 70, p. 695 (1948)] or using ordinary Raney nickel catalyst at 60°C. and 130 kg./cm.$^2$ pressure [*Bulletin de la société chimique de France* [5], Vol. 5, p. 1423 (1938)]; by chemical reduction of the corresponding substituted quinolines, e.g., with tin and hydrochloric acid [Wischnegradsky, *Chemische Berichte*, Vol. 13, p. 2400 (1880), and Fischer and Korner, ibid., Vol. 17, p. 765 (1884)]; by heating the appropriately substituted o-(3-chloropropyl)aniline [v. Braun and Steindorff, *Chemische Berichte*, Vol. 38, p. 583 (1905)]; by reacting o-toluidine with 1,3-dichloropropane to produce 8-methyl-1,2,3,4-tetrahydroquinoline (Pinkus, *Chemische Berichte*, Vol. 25, p. 2798 (1892)]; or by reductive ring closure of o-(2-acetylethyl)nitrobenzene to 2-methyl-1,2,3,4-tetrahydroquinoline [Jackson, *Chemische Berichte*, Vol. 14, p. 890 (1881)].

iv. The 1,2,3,4-tetrahydroisoquinolines, of the general formula:

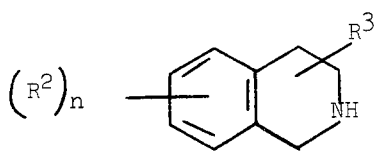

may be prepared by the cyclodehydration of the appropriately substituted β-phenethylamide to the corresponding 3,4-dihydroisoquinoline by heating the aforesaid amide in the presence of such dehydrating agents as phosphorus pentoxide, anhydrous zinc chloride, phosphorus oxychloride or phosphorus pentachloride, usually in an inert organic solvent like toluene, xylene or tetralin, followed by reduction in the usual manner, e.g., with sodium borohydride or with hydrogen and palladium-on-charcoal catalyst (the Bischler-Napieralski route); by condensation between the appropriately substituted benzaldehyde and 2-amino-acetaldehyde dialkyl acetal, followed by reduction of the Schiff base product, e.g., with hydrogen and platinum catalyst, and then hydrolysis/ring closure of the resulting N-benzylamino acetaldehyde dialkyl acetal in 6N hydrochloric acid solution, followed by selective reduction of the ring, e.g., with hydrogen and palladium-on-charcoal catalyst, to give the appropriate 1,2,3,4-tetrahydroisoquinoline [Bobbitt et al., *Journal of Organic Chemistry*, Vol. 30, p. 2247 (1965), and Bobbitt and Sih, ibid., Vol. 33, p. 856 (1968)].

v. The 2,3,4,5-tetrahydro-1H-benzo[b/c]azepines, of the general formulae:

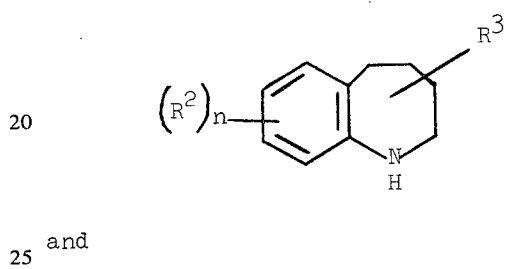

and

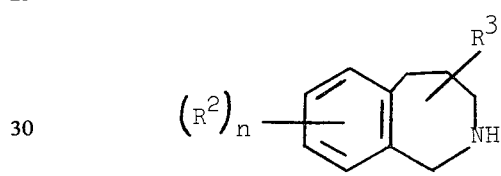

may be prepared by ring closure of the appropriately substituted haloamines, viz., o-(4-chlorobutyl)aniline [v. Braun and Bartsch, *Chemische Berichte*, Vol. 45, p. 3376 (1912)] and o-(3-chloropropyl)benzylamine [v. Braun and Zobel, ibid., Vol. 56, p. 690 (1923)], respectively. The 2,3,4,5-tetrahydro-1H-benzo[c]azepines may also be prepared through a modification of the Bischler-Napieralski route, using an appropriately substituted γ-phenylpropylamide in place of the β-phenethylamide [Kanaoka et al. *Tetrahedron Letters*, No. 35, p. 2419 (1964)].

vi. The 2,3,4,5-tetrahydro-1H-benzo[d]azepines, of the general formula:

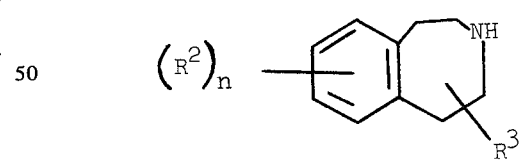

may be prepared by the reductive cyclization of the appropriately substituted o-xylylene dinitriles, e.g., by catalytic hydrogenation, in the presence of ammonia [Ruggli et al., *Helvetica Chimica Acta*, Vol. 18, p. 1388 (1935) and Ruggli and Staub, ibid., Vol. 20, p. 925 (1937)].

Needless to say, nitro-substituted indolines, isoinodolines, tetrahydroquinolines, tetrahydrosoquinolines and benzoazepines, etc., are all conveniently prepared from the corresponding desnitro compounds by means of conventional nitration procedures, e.g., by using a nitrating mixture consisting essentially of concentrated nitric and sulfuric acids, followed by, if necessary, the separation of the individual nitro-isomers from mixtures thereof.

The acids which are used to prepare the pharmaceutically-acceptable acid addition salts of the aforementioned aminoquinazoline base compounds of this invention are those which form non-toxic acid addition salts, i.e., salts containing pharmacologically acceptable anions, such as the hydrochloride, hydrobromide, hydriodide, sulfate or bisulfate, phosphate or acid phosphate, acetate, maleate, fumarate, oxalate, lactate, tartrate, citrate, gluconate, saccharate and p-toluenesulfonate salts.

The activity of the compounds of the present invention, as antihypertensive agents, is shown by their ability to lower the blood pressure of conscious hypertensive rats and dogs, when administered orally at dose levels within the range of 0.1 to 5.0 mg/kg. By virtue of their performance in such trials in animals, the preferred compounds of the invention, as previously indicated, are those in which the benzo-fused heterocyclic groups has the 1,2,3,4-tetrahydroisoquinoline nucleus, $(R^1)_m$ represents 6,7-di-lower alkoxy and $(R^2)_n$ represents 6,7-di-lower alkoxy, 7,8-di-lower alkoxy or 6-lower alkoxy-7-lower alkenoxy. Of particular value, as antihypertensive agents, have been found to be the compounds of Examples 1, 2, 8, 10, 13, 17, 28 and 29, respectively.

The compounds of the invention can be administered alone, but will generally be administered in admixture with a pharmaceutical carrier selected with regard to the intended route of administration and standard pharmaceutical practice. For instance, they may be administered orally in the form of tablets containing such excipients as starch or lactose, or in capsules either alone or in admixture with excipients, or in the form of elixirs or suspensions containing flavoring or coloring agents. They may also be injected parenterally, for example, intramuscularly, intravenously or subcutaneously. For purposes of parenteral administration, they are best used in the form of a sterile aqueous solution which may also contain other solutes like, for example, sufficient saline or glucose to make the solution isotonic.

The compounds of the invention can be administered to humans for the treatment of hypertension by either the oral or the parenteral routes, and may be administered orally at dosage levels approximately within the range of 0.05 mg. to 5 mg./day for an average adult patient (70 kg.), given in a single dose or up to three divided doses. Intravenous dosage levels would be expected to be about one-tenth of the daily oral dose, given in a single administration. Thus, for an average adult patient, individual oral doses in tablet or capsule form will be approximately in the range of from 0.02 mg. to 5 mg. of active compound. Variations will necessarily occur depending on the weight and condition of the subject being treated and the particular route of administration chosen.

EXAMPLE 1

4-Amino-6,7-dimethoxy-2-(6,7-dimethoxy-1,2,3,4-tetrahydroisoquinolin-2-yl)quinazoline A mixture of 4-amino-2-chloro-6,7-dimethoxyquinazoline (12.0 g., 0.05 mole), 6,7-dimethoxy-1,2,3,4-tetrahydroisoquinoline (9.6 g., 0.05 mole) and triethylamine (10.0 g., 0.10 mole) in ethanol (200 ml.) was heated in an autoclave at 160°C. for a period of 16 hours. The cooled brown solution was then filtered to remove sediment and evaporated in vacuo to dryness, affording a brown solid. Trituration of the latter in ethanol (200 ml.) then yielded the crude free base product, viz., 4-amino-6,7-dimethoxy-2-(6,7-dimethoxy-1,2,3,4-tetrahydroisoquinolin-2-yl)-quinazoline, as a white solid. This latter material was converted to the hydrochloride salt, which ultimately separated from aqueous methanol as the monohydrate (yield, 12.0 g.), m.p. 257°–258°C. with decomposition.

Anal. Calcd. for $C_{21}H_{24}N_4O_4 \cdot HCl \cdot H_2O$: C, 55.9; H, 6.0; N, 12.4; Cl, 7.9. Found: C, 56.1; H, 5.9; N, 12.3; Cl, 8.2.

EXAMPLE 2

4-Amino-6,7-dimethoxy-2-(7,8-dimethoxy-1,2,3,4-tetrahydroisoquinolin-2-yl(quinazoline The procedure described in Example 1 was repeated to prepare the above compound, except that 7,8-dimethoxy-1,2,3,4-tetrahydroisoquinoline was the reagent employed instead of the corresponding 6,7-dimethoxy compound. In this particular case, the final product was isolated as the hydrochloride salt, m.p. 253°–255°C.

Anal. Calcd. for $C_{21}H_{24}N_4O_4 \cdot HCl$: C, 58.3; H, 5.8; N, 12.9. Found: C, 58.5; H, 5.9; N, 12.6.

EXAMPLE 3

4-Amino-6,7-dimethoxy-2-(7-methoxy-1,2,3,4-tetrahydroisoquinolin-2-yl)quinazoline The procedure described in Example 1 was repeated to prepare the above compound, except that 7-methoxy-1,2,3,4-tetrahydroisoquinoline was the reagent employed (on the same molar basis as before) instead of the corresponding 6,7-dimethoxy compound. In this particular case, the final product was isolated as the hydrochloride monohydrate, m.p. >325°C.(dec.).

Anal. Calcd. for $C_{20}H_{22}N_4O_3 \cdot HCl \cdot H_2O$: C, 57.1; H, 6.0; N, 13.3; Cl, 8.4. Found: C, 56.6; H, 5.9; N, 12.9; Cl, 8.85.

EXAMPLE 4

4-Amino-6,7-dimethoxy-2-(7-hydroxy-6-methoxy-1,2,3,4-tetrahydroisoquinolin-2-yl)quinazoline The procedure described in Example 1 was repeated to prepare the above compound, except that 7-hydroxy-6-methoxy-1,2,3,4-tetrahydroisoquinoline was the reagent employed (on the same molar basis as before) instead of the corresponding 6,7-dimethoxy compounds. In this particular case, the final product was isolated as the hydrochloride salt, m.p. 224°–225°C.

Anal. Calcd. for $C_{20}H_{22}N_4O_4 \cdot HCl$: C, 57.35; H, 5.5; N, 13.4. Found: C, 56.9; H, 5.5; N, 13.2.

EXAMPLE 5

4-Amino-6,7-dimethoxy-2-(6-hydroxy-7-methoxy-1,2,3,4-tetrahydroisoquinolin-2-yl)quinazoline The procedure described in Example 1 was repeated to prepare the above compound, except that 6-hydroxy-7-methoxy-1,2,3,4-tetrahydroisoquinoline was the reagent employed (on the same molar basis as before) instead of the corresponding 6,7-dimethoxy compound. In this particular case, the product was isolated as the hydrochloride salt, m.p. 283°–284°C.

Anal. Calcd. for $C_{20}H_{22}N_4O_4 \cdot HCl$: C, 57.3; H, 5.5; N, 13.4. Found: C, 57.2; H, 5.6; N, 13.4.

EXAMPLE 6

4-Amino-6,7-dimethoxy-2-(6,7-ethylenedioxy-1,2,3,4-tetrahydroisoquinoline-2-yl)quinazoline The procedure described in Example 1 was repeated to prepare the above compound, except that 6,7-ethylenedioxy-1,2,3,4-tetrahydroisoquinoline was the reagent employed (on the same molar basis as before) instead of the corresponding 6,7-dimethoxy compound. In this particular case, the final product was isolated as the hydrochloride hemihydrate, m.p. 263°–264°C.

Anal. Calcd. for $C_{21}H_{22}N_4O_4 \cdot HCl \cdot 0.5H_2O$: C, 56.4; H, 5.2; N, 13.2. Found: C, 56.1; H, 4.9; N, 13.2.

EXAMPLE 7

4-Amino-6,7-dimethoxy-2-(5,6-dimethoxy-1,2,3,4-tetrahydroisoquinolin-2-yl)quinazoline The procedure described in Example 1 was repeated to prepare the above compound, except that 5,6-dimethoxy-1,2,3,4-tetrahydroisoquinoline was the reagent employed instead of the corresponding 6,7-dimethoxy compound. In this particular case, the final product was isolated as the hydrochloride hydrate with a 4:1 molecular ratio, respectively. The product melted at 253°C. (dec.).

Anal. Calcd. for $C_{21}H_{24}N_4O_4 \cdot HCl \cdot 0.25H_2O$: C, 57.7; H, 5.9; N, 12.8. Found: C, 57.3; H, 5.8; N, 12.9.

EXAMPLE 8

4-Amino-6,7-dimethoxy-2-(6-ethoxy-7-methoxy-1,2,3,4-tetrahydroisoquinolin-2-yl)quinazoline The procedure described in Example 1 was repeated to prepare the above compound, except that 6-ethoxy-7-methoxy-1,2,3,4-tetrahydroisoquinoline was the reagent employed (on the same molar basis as before) instead of the corresponding 6,7-dimethoxy compound. In this particular case, the product was isolated as the hydrochloride sesquihydrate, m.p. 254°–256°C.

Anal. Calcd. for $C_{22}H_{26}N_4O_4 \cdot HCl \cdot 1.5H_2O$: C, 56.0; H; 6.4; N, 11.4. Found: C, 56.4; H, 6.6; N, 11.4.

EXAMPLE 9

4-Amino-6,7-dimethoxy-2-(6-methoxy-7-n-propyloxy-1,2,3,4-tetrahydroisoquinolin-2-yl)quinazoline The procedure described in Example 1 was repeated to prepare the above compound, except that 6-methoxy-7-n-propyloxy-1,2,3,4-tetrahydroisoquinolin-2-yl)quinazoline was the reagent employed (on the same molar basis as before) instead of the corresponding 6,7-dimethoxy compound. In this particular case, the final product was isolated as the hydrochloride salt, m.p. 258°C.

Anal. Calcd. for $C_{23}H_{28}N_4O_4 \cdot HCl$: C, 59.9; H, 6.3; N, 12.2. Found: C, 60.0; H, 6.49; N, 12.1.

EXAMPLE 10

4-Amino-6,7-dimethoxy-2-(7-isopropyloxy-6-methoxy-1,2,3,4-tetrahydroisoquinolin-2-yl)quinazoline The procedure described in Example 1 was repeated to prepare the above compound, except that 7-isopropyloxy-6-methoxy-1,2,3,4-tetrahydroisoquinoline was the reagent employed (on the same molar basis as before) instead of the corresponding 6,7-dimethoxy compound. In this particular case, the final product was isolated as the hydrochloride monohydrate, m.p. >185°C. (dec.).

Anal. Calcd. for $C_{23}H_{28}N_4O_4 \cdot HCl \cdot H_2O$: C, 57.6; H, 6.3; N, 11.7. Found: C, 57.2; H, 6.0; N, 11.7.

EXAMPLE 11

4-Amino-6,7-dimethoxy-2-(5,6,7-trimethoxy-1,2,3,4-tetrahydroisoquinolin-2-yl)quinazoline The procedure described in Example 1 was repeated to prepare the above compound, except that 5,6,7-trimethoxy-1,2,3,4-tetrahydroisoquinoline was the reagent employed (on the same molar basis as before) instead of the corresponding 6,7-dimethoxy compound. In this particular case, the final product was isolated as the hydrochloride hydrae with a 4:1 molecular ratio, respectively (m.p. 295°C.).

Anal. Calcd. for $C_{22}H_{26}N_4O_5 \cdot HCl \cdot 0.25H_2O$: C, 56.5; H, 5.9; N, 12.0; Cl, 7.6. Found: C, 56.2; H, 5.7; N, 11.9; Cl, 7.7.

EXAMPLE 12

4-Amino-6,7-dimethoxy-2-(7-nitro-1,2,3,4-tetrahydroisoquinolin-2-yl)quinazoline

The procedure described in Example 1 was repeated to prepare the above compound, except that 7-nitro-1,2,3,4-tetrahydroisoquinoline was the reagent employed (on the same molar basis as before) instead of the corresponding 6,7-dimethoxy compound. In this particular case, the final product was isolated as the free base per se (m.p. 135°–137°C.).

Anal. Calcd. for $C_{19}H_{19}N_5O_4$: C, 59.8; H, 5.0; N, 18.4. Found: C, 60.1; H, 5.4; N, 18.3.

EXAMPLE 13

4-Amino-2-(6,7-diethoxy-1,2,3,4-tetrahydroisoquinolin-2-yl)-6,7-dimethoxyquinazoline The procedure described in Example 1 was repeated to prepare the above compound, except that 6,7-diethoxy-1,2,3,4-tetrahydroisoquinoline was the reagent employed (on the same molar basis as before) instead of the corresponding 6,7-dimethoxy compound. In this particular case, the final product was isolated as the hydrochloride dihydrate, m.p. 258°–259°C.

Anal. Calcd. for $C_{23}H_{28}N_4O_4 \cdot HCl \cdot 2H_2O$: C, 55.5; H, 6.1; N, 11.3. Found: C, 55.7; H, 6.2; N, 11.6.

EXAMPLE 14

4-Amino-6,7-dimethoxy-2-(8-hydroxy-7-methoxy-1,2,3,4-tetrahydroisoquinolin-2-yl)quinazoline The procedure described in Example 1 was repeated to prepare the above compound, except that 8-hydroxy-7-methoxy-1,2,3,4-tetrahydroisoquinoline was the reagent employed (on the same molar basis as before) instead of the corresponding 6,7-dimethoxy compound. In this particular case, the final product was isolated as the hydrochloride sesquihydrate, m.p. 255°–260°C.

Anal. Calcd. for $C_{20}H_{22}N_4O_4 \cdot HCl \cdot 1.5H_2O$: C, 53.86; H, 5.88; N, 12.56. Found: C, 53.73; H, 5.53; N, 12.81.

EXAMPLE 15

4-Amino-6,7-dimethoxy-2-(6,7,8-trimethoxy-1,2,3,4-tetrahydroisoquinolin-2-yl)quinazoline The procedure described in Example 1 was repeated to prepare the above compound, except that 6,7,8-trimethoxy-1,2,3,4-tetrahydroisoquinoline was the reagent employed (on the same molar basis as before) instead of the corresponding 6,7-dimethoxy compound. In this particular case, the final product was isolated as hydrochloride monohydrate, m.p. 252°–253°C.

Anal. Calcd. for $C_{22}H_{26}N_4O_5 \cdot HCl \cdot H_2O$: C, 54.90; H, 5.49; N, 11.65. Found: C, 54.41; H, 5.49; N, 11.49.

EXAMPLE 16

4-Amino-2-(7-n-butyloxy-6-methoxy-1,2,3,4-tetrahydroisoquinolin-2-yl)-6,7-dimethoxyquinazoline The procedure described in Example 1 was repeated to prepare the above compound, except that 7-n-butyloxy-6-methoxy-1,2,3,4-tetrahydroisoquinoline was the reagent employed (on the same molar basis as before) instead of the corresponding 6,7-dimethoxy compound. In this particular case, the final product was isolated as the hydrochloride hemihydrate, m.p. 249°–250°C.

Anal. Calcd. for $C_{24}H_{30}N_4O_4 \cdot HCl \cdot 0.5H_2O$: C, 59.56; H, 6.46; N, 11.58. Found: C, 59.10; H, 6.49; N, 11.49.

EXAMPLE 17

4-Amino-6,7-dimethoxy-2-(6,7-dimethoxy-1-methyl-1,2,3,4-tetrahydroisoquinolin-2-yl)quinazoline The procedure described in Example 1 was repeated to prepare the above compound, except that 6,7-dimethoxy-1-methyl-1,2,3,4-tetrahydroisoquinoline was the reagent employed (on the same molar basis as before) instead of the corresponding 1-demethyl compound. In this particular case, the final product was isolated as the hydrochloride monohydrate, m.p. 211°–212°C.

Anal. Calcd. for $C_{22}H_{26}N_4O_4 \cdot HCl \cdot H_2O$: C, 56.83; H, 6.07; N, 12.04. Found: C, 56.48; H, 5.99; N, 11.72.

EXAMPLE 18

4-Amino-2-(6,7-dimethoxy-1,2,3,4-tetrahydroisoquinolin-2-yl)-6,7,8-trimethoxyquinazoline The procedure described in Example 1 was repeated to prepare the above compound, except that 4-amino-2-chloro-6,7,8-trimethoxquinazoline was the starting material employed (on the same molar basis as before) in place of the corresponding 6,7-dimethoxy compound. In this particular instance, the final product was isolated as the free base compound, m.p. 204°C.

Anal. Calcd. for $C_{22}H_{26}N_4O_5$: C, 61.95; H, 6.14; N, 13.14. Found: C, 61.83; H, 6.18; N, 12.95.

EXAMPLE 19

4-Amino-2-(7-methoxy-1,2,3,4-tetrahydroisoquinolin-2-yl)-6,7,8-trimethoxyquinazoline The procedure described in Example 1 was followed to prepare the above compound, starting from 4-amino-2-chloro-6,7,8-trimethoxyquinazoline and using 7-methoxy-1,2,3,4-tetrahydroisoquinoline as the reagent of choice on the same molar basis as before. In this particular case, the final product was isolated as the hydrochloride salt m.p. 236°C.

Anal. Calcd. for $C_{21}H_{24}N_4O_4 \cdot HCl$: C, 58.26; H, 5.82; N, 12.94. Found: C, 57.86; H, 5.83; N, 13.51.

EXAMPLE 20

4-Amino-2-(7,8-dimethoxy-1,2,3,4-tetrahydroisoquinolin-2-yl)-6,7,8-trimethoxyquinazoline The procedure described in Example 1 was followed to prepare the above compound, starting from 4-amino-2-chloro-6,7,8-trimethoxyquinazoline and using 7,8-dimethoxy-1,2,3,4-tetrahydroisoquinoline as the reagent of choice on the same molar basis as before. In this particular instance, the final product was isolated as the free base compound, m.p. 190°C.

Anal. Calcd. for $C_{22}H_{26}N_4O_5$: C, 61.95; H, 6.14; N, 13.14. Found: C, 61.62; H, 6.20; N, 12.59.

EXAMPLE 21

4-Amino-6,7,8-trimethoxy-2-(5,6,7-trimethoxy-1,2,3,4-tetrahydroisoquinolin-2-yl)quinazoline The procedure described in Example 1 was followed to prepare the above compound, starting from 4-amino-2-chloro-6,7,8-trimethoxyquinazoline and using 5,6,7-trimethoxy-1,2,3,4-tetrahydroisoquinoline as the reagent of choice on the same molar basis as before. In this particular instance, the final product was obtained as the free base compound, m.p. 193°–195°C.

Anal. Calcd. for $C_{23}H_{28}N_4O_6$: C, 60.51; H, 6.18; N, 12.27. Found: C, 60.28; H, 5.89; N, 12.36.

EXAMPLE 22

4-Amino-6,7-diethoxy-2-(6,7-dimethoxy-1,2,3,4-tetrahydroisoquinolin-2-yl)-quinazoline The procedure described in Example 1 was repeated to prepare the above compound, except that 4-amino-2-chloro-6,7-diethoxyquinazoline was the starting material employed (on the same molar basis as before) in place of the corresponding 6,7-dimethoxy compound. In this particular case, the final product was isolated as the hydrochloride hemihydrate, m.p. 249°–251°C. (dec.).

Anal. Calcd. for $C_{23}H_{28}N_4O_4 \cdot HCl \cdot 0.5H_2O$: C, 58.78; H, 6.22; N, 11.92. Found: C, 59.13; H, 6.04, N, 12.19.

EXAMPLE 23

4-Amino-6,7,diethoxy-2-(7-ethoxy-6-methoxy-1,2,3,4-tetrahydroisoquinolin-2-yl)quinazoline The procedure described in Example 1 was followed to prepare the above compound, starting from 4-amino-2-chloro-6,7-diethoxyquinazoline and using 7-ethoxy-6-methoxy-1,2,3,4-tethrahydroisoquinoline as the reagent of choice on the same molar basis as before. In this particular case, the final product was isolated as the hydrochloride salt, m.p. 235°–237°C. (dec.).

Anal. Calcd. for $C_{24}H_{30}N_4O_4 \cdot HCl$: C, 60.69; H, 6.58; N, 11.80. Found: C, 60.45; H, 6.63; N, 12.25.

EXAMPLE 24

4-Amino-7-benzyloxy-6-methoxy-2-(6,7-dimethoxy-1,2,3,4-tetrahydroisoquinolin-2-yl)quinazoline The procedure described in Example 1 was repeated to prepare the above compound, except that 4-amino-2-chloro-7-benzyloxy-6-methoxyquinazoline was the starting material employed (on the same molar basis as before) in place of the corresponding 6,7-dimethoxy compound. In this particular case, the final product was isolated as the hydrochloride monohydrate, m.p. 265°–268°C. (dec.).

Anal. Calcd. for $C_{27}H_{28}N_4O_4 \cdot HCl \cdot H_2O$: C, 61.53; H, 5.93, N, 10.63. Found: C, 61.81; H, 5.69, N, 11.09.

EXAMPLE 25

4-Amino-2-(6,7-dimethoxy-1,2,3,4-tetrahydroisoquinolin-2-yl)-6,7-ethylenedioxyquinazoline The procedure described in Example 1 was repeated to prepare the above compound, except that 4-amino-2-chloro-6,7-ethylenedioxyquinazoline was the starting material employed (on the same molar basis as before) in place of the corresponding 6,7-dimethoxy compound. In this particular case, the final product was isolated as the hydrochloride hydrate with a 4:1 molecular ratio, respectively (m.p. 303°–306°C.).

Anal. Calcd. for $C_{21}H_{22}N_4O_4 \cdot HCl \cdot 0.25H_2O$: C, 57.90; H, 5.44; N, 12.87. Found: C, 57.97; H, 5.66; N, 13.20.

EXAMPLE 26

4-Amino-6,7-dimethoxy-2-(7,8-dimethoxy-2,3,4,5-tetrahydro-1H-benzo c]azepin-2-yl)quinazoline The procedure described in Example 1 was repeated to prepare the above compound, except that 7,8-dimethoxy-2,3,4,5-1H-2-benzo[c]azepine was the reagent employed (on the same molar basis as before) instead of 6,7-dimethoxy-1,2,3,4-tetrahydroisoquinoline. In this particular instance, the final product was isolated as the free base compound, m.p. 122°–124°C.

Anal. Calcd. for $C_{22}H_{26}N_4O_4$: C, 64.4; H, 6.4; N, 13.6. Found: C, 64.3; H, 6.5; N, 13.8.

EXAMPLE 27

4-Amino-6,7-dimethoxy-2-(7,8-dimethoxy-2,3,4,5-tetra-1-H-benzo[d]azepin-3-yl)quinazoline The procedure described in Example 1 was repeated to prepare the above compound, except that 7,8-dimethoxy-2,3,4,5-1H-3-benzo[d]azepine was the reagent employed (on the same molar basis as before) instead of 6,7-dimethoxy-1,2,3,4-tetrahydroisoquinoline. In this particular instance, the final product was isolated as the free base compound, m.p. 211°–212°C.

Anal. Calcd. for $C_{22}H_{26}N_4O_4$: C, 64.4; H, 6.4; N, 13.6. Found: C, 64.3; H, 6.5; N, 13.8.

EXAMPLE 28

4-Amino-6,7-dimethoxy-2-(7-ethoxy-6-methoxy-1,2,3,4-tetrahydroisoquinolin-2-yl)quinazoline To a stirred solution of the final product of Example 4 dissolved in methanol, viz., 4-amino-6,7-dimethoxy-2-(7-hydroxy-6-methoxy-1,2,3,4-tetrahydroisoquinolin-2-yl)quinazoline hydroxhloride (0.10g., 0.00025 mole) in methanol, there was added methanolic sodium methoxide solution (2.5ml.) that had first been prepared from freshly-cut sodium (2.3g.) and anhydrous methanol (500 ml.), i.e., 0.0005 mole of sodium methoxide. After the addition was complete, stirring was continued for a one-half hour period and the solvent was thereafter removed by means of evaporation under reduced pressure. The residue so obtained was dissolved in dry dimethylacetamide (10 ml.) and to this resulting solution, there was then added a solution (2.5 ml.) consisting of ethyl iodide (1.56g.) in dry dimethylacetamide (100 ml.) i.e., 0.00025 mole of ethyl iodide. The final mixture was stirred at room temperature (~25°C.) for a period of 16 hours. Evaporation of the resulting mixture then gave the crude free base product, which was subsequently converted to the hydrochloride salt in the usual manner and then recrystalized from methanol yielding the final product as the hydrochloride monohydrate, m.p. 258°–260°C.

Anal. Calcd. for $C_{22}H_{26}N_4O_4 \cdot HCl \cdot H_2O$: C, 56.9; H, 6.3; N, 12.1. Found: C, 56.7; H, 6.1N, 12.2.

EXAMPLE 29

2-(7-Allyloxy-6-methoxy-1,2,3,4-tetrahydroisoquinolin-2-yl)-4-amino-6,7-dimethoxyquinazoline The procedure described in Example 28 was repeated to prepare the above compound, except that allyl bromide was the reagent employed (on the same molar basis as before) instead of ethyl iodide. In this particular case, the final product was isolated as the hydrochloride monohydrate, m.p. 215°C.

Anal. Calcd. for $C_{23}H_{26}N_4O_4 \cdot HCl \cdot H_2O$: C, 57.92; H, 5.91; N, 11.75. Found: C, 58.03; H, 5.65; N, 12.04.

EXAMPLE 30

4-Amino-6,7-dimethoxy-2-[6-methoxy-7-(2-pyridyloxy)-1,2,3,4-tetrahydroisoquin-2-yl]quinazoline The procedure described in Example 28 was repeated to prepare the above compound, except that 2-chloropyridine was the reagent employed (on the same molar basis as before) instead of ethyl iodide. In this particular case, the final product was isolated as the hydrochloride monohydrate, m.p. 195°–196°C.

Anal. Calcd. for $C_{25}H_{25}N_5O_4 \cdot HCl \cdot H_2O$: C, 58.40, H, 5.49; N, 13.63. Found: C, 57.90; H, 5.13; N, 13.67.

EXAMPLE 31

4-Amino-6,7-dimethoxy-2-(8-ethoxy-7-methoxy-1,2,3,4-tetrahydroisoquinolin-2-yl)quinazoline The procedure described in Example 28 was repeated to prepare the above compound, except that 4-amino-6,7-dimethoxy-2-(8-hydroxy-7-methoxy-1,2,3,4-tetrahydroisoquinolin-2-yl)-quinazoline hydrochloride sesquihydrate (the product of Example 14) was the starting material employed (on the same molar basis as before) in place of the corresponding 6-hydroxy compound. In this particular case, the final product was isolated as the hydrochloride monohydrate, m.p. 245°C. (dec.).

Anal. Calcd. for $C_{22}H_{26}N_4O_4 \cdot HCl \cdot H_2O$: C, 56.83; H, 6.29; N, 12.05. Found: C, 56.16; H, 5.84; N, 11.79.

EXAMPLE 32

4-Amino-2-(7-amino-1,2,3,4-tetrahydroisoquinolin-2-yl)-6,7-dimethoxyquinazoline

4-Amino-6,7-dimethoxy-2-(7-nitro-1,2,3,4-tetrahydroisoquinolin-2-yl)quinazoline (2.0 g.), the product of Example 12, was slurried in 6N hydrochloric acid solution (100 ml.) and the resulting mixture was cooled with stirring to 0°C. A solution of stannous chloride (20.0 g.) in 6N hydrochloric acid (20 ml.) was then added, and the reaction mixture was heated gradually to 70°C., followed by cooling to give a white solid precipitate. The latter material was collected by means of suction filtration and thereafter recrystallized from ethanol to afford 1.0 g. of pure final product as the dihydrochloride dihydrate, m.p. 265°–266°C.

Anal. Calcd. for $C_{19}H_{21}N_5O_2 \cdot 2HCl \cdot 2H_2O$: C, 49.5; H, 5.5; N, 15.2; Cl, 15.4. Found: C, 49.8; H, 5.3; N, 15.0; Cl, 14.4.

EXAMPLE 33

2-(7-Acetamido-1,2,3,4-tetrahydroisoquinolin-2-yl)-4-amino-6,7-dimethoxyquinazoline To a solution of the free base compound of the product of Example 32 in dichloromethane, viz, 4-amino-2-(7-amino-1,2,3,4-tetrahydroisoquinolin-2-yl)-6,7-dimethoxyquinazoline (5.0g.) dissolved in dichloromethane (50 ml.) containing triethylamine (1.3 ml.), there was added in one small portion acetyl chloride (1.0 ml), and the resulting mixture was stirred for 3 hours and then evaporated to dryness while under reduced pressure. The solid residue so obtained was recrystallized twice from isopropanol and then once (using decolorizing charcoal) from ethanol to yield 2.0 g. of final product as the hydrochloride sesquihydrate, m.p. 243°–244°C.

Anal. Calcd. for $C_{21}H_{23}N_5O_3 \cdot HCl \cdot 1.5H_2O$: C, 55.2; H, 5.9; N, 15.3. Found: C, 55.2; H, 5.5; N, 14.9.

EXAMPLE 34

4-Amino-6,7-dimethoxy-2-[7-(2-furoamido)-1,2,3,4-tetrahydroisoquinolin-2-yl]quinazoline The procedure described in Example 33 was repeated to prepare the above compound, except that 2-furoyl chloride was the reagent employed (on the same molar basis as before) instead of acetyl chloride. In this particular case, the final product was isolated as hydrochloride monohydrate, m.p. 244°–245°.

Anal. Calcd. for $C_{24}H_{23}N_5O_4 \cdot HCl \cdot H_2O$: C, 57.6; H, 5.2; N, 14.0. Found: C, 57.5; H, 4.9; N, 14.0.

EXAMPLE 35

4-Amino-(7-benzenesulfonamindo-1,2,3,4-tetrahydroisoquinolin-2-yl)-6,7-dimethoxyquinazoline The procedure described in Example 33 was repeated to prepare the above compound, except that benzenesulfonyl chloride was the reagent employed (on the same molar basis as before) instead of acetyl chloride. In this particular case, the final product was isolated as the hydrochloride monohydrate, m.p. 255°–257°C.

Anal. Calcd. for $C_{25}H_{25}N_5O_4S$: C, 54.9; H, 5.2; N, 12.9. Found: C, 55.1; H, 4.8; N, 13.4.

4-Amino-6,7-dimethoxy-2-(7-ethoxycarbonylamino-1,2,3,4-tetrahydroisoquinolin-2-yl)quinazoline

EXAMPLE 36

A mixture of 4-amino-2-(7-amino-1,2,3,4-tetrahydroisoquinolin-2-yl)-6,7-dimethoxyquiinazoline (2.5g), ethyl chloroformate (1.5g.) and triethylamine (0.8 ml.) dissolved in chloroform (50 m.) was refluxed with stirring for a period of 18 hours. At the end of this time, the solvent was removed from the mixture by means of evaporation under reduced pressure to afford a tacky brown solid as residue. This latter material was then basified by the gradual addition of dilute aqueous sodium hydroxide solution thereto, and the resulting mixture was next extracted with fresh methylene chloride, with the organic layer being ultimately evaporated to near dryness in vacuo. Chromatography of the residual oil (2.5 g.) through a Florisil column ("Florisil" is the registered trademark name of the Floridin Company of Tallahassee, Florida for a synthetic magnesia-silica gel consisting of hard, white granules), using a 10% $CH_3OH/CHCl_3$ solution as eluant, then gave 12 collected fractions, of which the last six were combined and subsequently evaporated in vacuo to dryness. The resulting grey gum (1.0 g.) was then converted into the hydrochloride salt in the usual manner and the salt product thus obtained was ultimately recrystallized four times from isopropanol to yield 0.4 g of pure final product as the hydrochloride monohydrate in the form of as white crystals, melting at 210°C. with decomposition.

Anal. Calcd. for $C_{22}H_{25}N_5O_4 \cdot HCl \cdot H_2O$: C, 55.28; H, 5.95; N, 14.65. Found: C, 55.00; H, 5.75; N, 14.94.

EXAMPLE 37

4-Amino-2-(6,7-dimethoxy-1,2,3,4-tetrahydroisoquinolin-2-yl)-7-hydroxy-6-methoxyquinazoline A solution of the final product of Example 24, viz., 4-amino-7-benzyloxy-2-(6,7-dimethoxy-1,2,3,4-tetrahydroisoquinolin-2-yl)-6-methoxyquinazoline hydrochloride monohydrate, in 50% aqueous acetic acid (100 ml.) was hydrogenated in the presence of a small quantity of palladium-on-charcoal catalyst at 15 p.s.i. pressure and at room temperature (~25°C.) until the theroetical uptake of hydrogen had been achieved. The catalyst and other solid residues were then removed from the reaction mixture by means of filtration and the filtrate thereafter evaporated in vacuo to dryness with the solid residue so obtained being finally recrystallized from ethanol to afford pure final product as the hydrochloride monohydrate, m.p. 254°–256°C.

Anal. Calcd. for $C_{20}H_{22}N_4O_4 \cdot HCl \cdot H_2O$: C, 54.98; H, 5.77; N, 12.82. Found: C, 55.27; H, 5.40; N, 13.00.

EXAMPLE 38

4-Amino-6,7-dimethoxy-2-(5,6-dimethoxyisoindolin-2-yl)quinazoline

A. 4,5-Di(chloromethyl)veratrole (11.75 g.) and benzyhdrylamine (27.45 g) were refluxed in chloroform (400 ml.) for 40 hours. The cooled reaction mixture was then diluted with diethyl ether (800 ml.), and the resulting precipitate of benzhydrylamine hydrochloride (20.2 g.) was removed by filtration and washed with diethyl ether (2 × 100 ml.). The combined filtrate and washings were then evaporated to dryness to give an oil (20.0 g.), which on subsequent trituration with a 50% mixture (30 ml.) of diethyl ether and petroleum ether (b.p. 40°–60°C.) gave a solid product (14.0 g.) that later crystallized from di-isopropyl ether to afford pure 2-benzhydryl-5,6-dimethoxyisoindoline (9.9 g.), mp. 126°–8°C.

Anal. Calcd. for $C_{23}H_{23}NO_2$: C, 80; H, 6.7; N, 4.0. Found: C, 80.3; H, 6.8; N, 3.8.

B. A solution of the product of (A) in ethanolic hydrochloric acid, viz., 2-benzhydryl-5,6-dimethoxyisolindoline (1.73 g.) dissolved in ethanol (100 ml.) containing 1N aqueous hydrochloric acid (5.0 ml), was hydrogenated over 5% palladium-on-charcoal catalyst (1.0 g.) for a period of three hours under 50 p.s.i. pressure and a temperature of 60°C. The catalyst was next removed by filtration and diethyl ether (200 ml.) was added to the resulting filtrate, thus precipitating 5,6-dimethoxyisoindoline hydrochloride (0.80 g.), m.p. 286°–7°C.

Anal. Calcd. for $C_{10}H_{13}NO_2 \cdot HCl$: C, 55.7 ; H, 6.5; N, 6.5. Found: C, 55.5; H, 6.5; N, 6.6.

C. A mixture consisting of the product of (B), viz., 5,6-dimethoxyisoindoline hydrochloride (1.9g.), together with 4-amino-2-chloro-6,7-dimethoxyquinazoline (2.16 g.) and N-ethylpiperidine (3.11 g.) all dissolved in 2-ethoxyethanol (60 ml.) was refluxed for a period of 6 hours, followed by cooling to room temperature (~25°C.). The resulting precipitate of 4-amino-6,7-dimethoxy-2-(5,6-dimethoxyisoindolin-2-yl)quinazoline hydrochloride (3.50 g., m.p. 318°C.) was then shaken with a mixture consisting of dichloromethane (1000 ml.) and 0.5N sodium hydroxide solution in 50% aqueous ethanol (200 ml.). On separation and utimate evaporation of the organic layer there was obtained a solid material (2.4 g.), which was subsequently crystallized from ethanol to give pure final product as the free base compound (yield, 1.40g.), m.p. 264°–6°C.

Anal. Calcd. for $C_{20}H_{22}N_4O_4$: C, 62.8; H, 5,8; N, 14.6. Found: C, 63.0; H, 5.9; N, 14.9.

EXAMPLE 39

2-Amino-6,7-dimethoxy-4-(6,7-dimethoxy-1,2,3,4-tetrahydroisoquinolin-2-yl)quinazoline A. To a chilled solution ofo 2,4-dichloro-6,7-dimethoxywuinsxolinr (15.5 g.) dissolved in dimethylacetamide (50 ml.), there was added a solution consisting of 6,7-dimethoxy-1,2,3,4-tetrahydroisoquinoline (11.5 g.) and triethylamine (20 ml.) also dissolved in dimethylacetamide (50 ml.). The resulting mixture was then allowed to stand at room temperature (~25°C.) overnight, i.e., for a period of approximately 16 hours at ambient temperatures. At the end of this time, the precipitate of triethylamine hydrochloride which formed in situ was removed by filtration and the filtrate was evaportated in vacuo to dryness, thus affording 25 g. of an off-white solid as residual product. The latter material was subsequently recrystallized from methanol to afford 8.0 g. of pure 2-chloro-6,7-dimethoxy-4-(6,7-dimethoxy-1,2,3,4-tetrahydroisoquinolin-2-yl)quinazoline, m.p. 128°C.

Anal. Calcd. for $C_{21}H_{22}ClN_3O_4$: C, 60.75; H, 5.33; N, 10.1. Found: C, 61.16; H, 5.52; N, 9.91.

B. The product of (A), viz, 2-chloro-6,7-dimethoxy-4-(6,7-dimethoxy-1,2,3,4-tetrahydroisoquinolin-2-yl)quinazoline (5.0 g.) and a saturated solution of ammonia in ethanol (60 ml.) were heated together in an autoclave at 100°C. for a period of approximately 16 hours. After the reaction mixture had been allowed to cool to room temperature (~26°C.), the solvent was removed by means of evaporation under reduced pressure and the resulting brown residue (5.0 g.) was partitioned between methylene chloride and water. The separated organic layer thus obtained was then evaported in vacuo and the residue (3.0 g.) was subsequently converted into the hydrochloride salt by conventional means. Recrystallization of the crude material from a mixture of e thanol and isopropanol then afforded 1.0 g. of pure final product as the hydrochloride hemihydrate, m.p. 245°C.

Anal. Calcd. for $C_{21}N_{24}N_4O_4.HCl.0.5H_2O$: C, 57.10; H, 5.93; N, 12.68. Found: C, 57.34; H, 5.68; N, 13.02.

EXAMPLE 40

2-Amino-6,7-dimethoxy-4-(5,6,7-trimethoxy-1,2,3,4-tetrahydroisoquinolin-2-yl)quinazoline The procedure described in Example 39 was repreated to prepare the above compound, except that 5,6,7-trimethoxy-1,2,3,4-tetrahydroisoquinoline was the reagent employed (on the same molar basis as before) instead of the corresponding 6,7-dimethoxy compound. In this particular case, the final product was isolated as the hyrochloride salt, m.p. 310°C.

Anal. Calcd. for $C_{22}H_{26}N_4O_5.HCl$: C, 57.07; H, 5.88; N, 12.00. Found: C, 57.43; H, 5.78; N, 11.48.

EXAMPLE 41

A dry solid pharmaceutical composition is prepared by combining the following materials together in the proportions by weight specified below:

| | |
|---|---|
| 4-Amino-6,7-dimethoxy-2-(7,8-dimethoxy-1,2,3,4-tetrahydroisoquinolin-2-yl)quinazoline hydrochloride | 2 |
| Avicel | 74 |
| Lactose | 20 |
| Alginic acid | 3 |
| Magnesium stearate | 1 |

After the dried composition is thoroughly blended, tablets are punched from the resulting mixture, each tablet being of such size that it contains 2 mg. of the active ingredient. Other tablets are also prepared in a similar fashion containing 0.5, 1 and 4 mg. of the active ingredient, respectively, by merely using the appropriate amount of the aminoquinazoline compound in each case.

EXAMPLE 42

A dry solid pharmaceutical composition is prepared by combining the following materials together in the proportion by weight indicated below:

| | |
|---|---|
| 4-Amino-6,7-dimethoxy-2-(6,7-diethoxy-1,2,3,4-tetrahydro-isoquinolin-2-yl)quinazoline hydrochloride dihydrate | 1 |
| Lactose | 77 |
| Maize starch | 20 |
| Magnesium stearate | 2 |

The dried solid mixture so prepared is then thoroughly agitated so as to obtain a powdered product that is completely uniform in every respect. Hard-filled gelatin capsules containing this pharmaceutical composition are then prepared, employing a sufficient quantity of material in each instance so as to provide each capsule with 1 mg. of the active ingredient.

What is claimed is:
1. A compound of the formula:

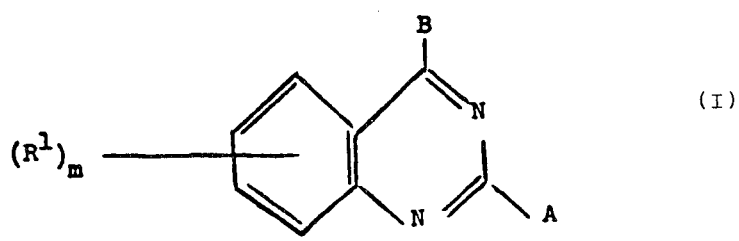

and the pharmaceutically-acceptable acid addition salts thereof, wherein $(R^1)_m$ represents from one to three substituents, each $R^1$ being hydroxyl, benzyloxy or lower alkoxy and m being an integer of from 1 to 3, or two of the moieties $R^1$ when taken together form lower alkylenedioxy directly attached to adjacent positions of the benzene-ring portion of the quinazoline nucleus; and one of A and B represents amino, while the other represents benzo-fused heterocyclic ring moiety of the formula:

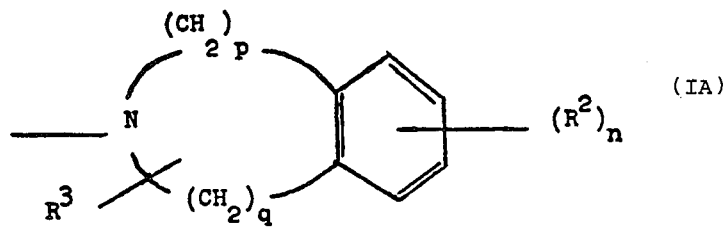

(IA)

wherein $(R^2)_n$ represents from one to three substituents, each $R^2$ being hydroxyl, lower alkoxy, lower alkenoxy, phenoxy, pyridyloxy, amino, lower alkanoamido, benzenesulfonamido, furoamido or lower alkoxycarbonylamino, n being an integer of from 1 to 3, with the proviso that n can only be 1 when $R^2$ is amino, lower alkanoamido, benzenesulfonamido, furoamido or lower alkoxycarbonylamino; two of the moieties $R^2$ when taken together form lower alkylenedioxy directly attached to adjacent positions of the benzene-ring portion of the benzo-fused heterocyclic ring moiety; $R^3$ is hydrogen or lower alkyl directly attached to any one of the substitutable carbon atoms of the heterocyclic portion of the benzo-fused heterocyclic ring moiety; and p and q are each 0 to 3 with the proviso that p plus q equals 3.

2. A compound as claimed in claim 1 wherein A represents the benzo-fused heterocyclic ring moiety of formula (IA) and B is amino.

3. A compound as claimed in claim 2 wherein the benzo-fused heterocyclic ring moiety of formula (IA) has the 1,2,3,4-tetrahydroisoquinoline nucleus where p is 2 is 1.

4. A compound as claimed in claim 1 wherein $(R^1)_m$ represents two substituents, each $R^1$ being lower alkoxy and m being equal to 2, with said $(R^1)_m$ being 6,7-di-lower alkoxy.

5. A compound as claimed in claim 3 wherein $(R^2)_n$ on the 1,2,3,4-tetrahydroisoquinoline nucleus represents two substituents, each $R^2$ being lower alkoxy and n being equal to 2, with said $(R^2)_m$ being 6,7-di-lower alkoxy.

6. A compound as claimed in claim 3 wherein $(R^2)$ on the 1,2,3,4-tetrahydroisoquinoline nucleus represents two substituents, each $R^2$ being lower alkoxy and n being equal to 2, with said $(R^2)_n$ being 7,8-di-lower alkoxy.

7. A compound as claimed in claim 3 wherein $(R^2)_n$ on the 1,2,3,4-tetrahydroisoquinoline nucleus represents two substituents, $R^2$ being lower alkoxy and lower alkenoxy, respectively, n being equal to 2, with said $(R^2)_n$ being 6-lower alkoxy-7-lower alkenoxy.

8. A compound as claimed in claim 4 wherein $(R^1)_m$ is 6,7-dimethoxy.

9. A compound as claimed in claim 6 wherein $(R^2)_n$ is 7,8-dimethoxy.

10. A compound as claimed in claim 1 of the formula:

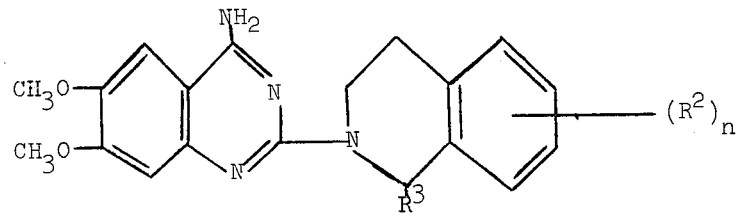

wherein $(R^2)_n$ represents 6,7-di-lower alkoxy, 7,8-di-lower alkoxy or 6-methoxy-7-allyloxy and $R_3$ is hydrogen or methyl.

11. A compound as claimed in claim 10 wherein $(R^2)_n$ represents 6,7-di-lower alkoxy and $R^3$ is hydrogen.

12. A compound as claimed in claim 10 wherein $(R^2)_n$ represents 7,8-di-Lower alkoxy and $R^3$ is hydrogen.

13. The compound as claimed in claim 10 wherein $(R^2)_n$ is 6-methoxy-7-allyloxy and $R^3$ is hydrogen.

14. The compound as claimed in claim 10 wherein $(R^2)_n$ is 6,7-dimethoxy and $R^3$ methyl.

15. The compound as claimed in claim 11 wherein $(R^2)_n$ is 6,7-dimethoxy.

16. The compound as claimed in claim 11 wherein $(R^2)_n$ is 6,7-diethoxy.

17. The compound as claimed in claim 11 wherein $(R^2)_n$ is 6-ethoxy-7-methoxy.

18. The compound as claimed in claim 11 wherein $(R^2)_n$ is 7-ethoxy-6-methoxy.

19. The compound as claimed in claim 11 wherein $(R^2)_n$ is 7-isopropyloxy-6-methoxy.

20. The compound as claimed in claim 12 wherein $(R^2)_n$ is 7,8-dimethoxy.

* * * * *